US00PP31224P2

(12) United States Plant Patent
Hansen

(10) Patent No.: US PP31,224 P2
(45) Date of Patent: Dec. 10, 2019

(54) ***HEUCHERA* PLANT NAMED 'PINK PANTHER'**

(50) Latin Name: ***Heuchera* hybrid**
Varietal Denomination: Pink Panther

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 16/350,944

(22) Filed: Feb. 1, 2019

(51) Int. Cl.
*A01H 5/00* (2018.01)
*A01H 6/80* (2018.01)

(52) U.S. Cl.
USPC ..... Plt./440

(58) Field of Classification Search
USPC ..... Plt./440
CPC ..... A01H 5/00; A01H 6/80
See application file for complete search history.

*Primary Examiner* — Annette H Para

(57) ABSTRACT

The new and distinct hybrid of *Heuchera* plant named *Heuchera* 'Pink Panther' with large distinct foliage. The new plant is vigorous and produces large broadly-mounded clumps.

1 Drawing Sheet

Botanical denomination: *Heuchera* hybrid.
Variety denomination: 'Pink Panther'.

STATEMENT REGARDING PRIOR DISCLOSURES UNDER 37 CFR 1.77(b)(6)

The first public disclosure of the claimed plant, in the form of a photograph and brief description on a website operated by Walters Gardens, Inc. on Feb. 1, 2018. The claimed plant was first sold on Jun. 4, 2018 by Walters Gardens, Inc., who obtained the plant and all information relating thereto, from the inventor. No plants of *Heuchera* 'Pink Panther' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Coral Bells in the Saxifragaceae family and given the cultivar name of 'Pink Panther'. *Heuchera* 'Pink Panther' was hybridized by the inventor on Apr. 22, 2013 at a wholesale perennial nursery in Zeeland, Mich., USA. The seed or female parent was the proprietary unreleased hybrid known by the breeder code 12-490-01 and the pollen or male parent was the proprietary unreleased hybrid known by the breeder code K11-52-15.

*Heuchera* 'Pink Panther' was first selected in the summer of 2014 and assigned the breeder code 13-802-1 through the remaining evaluation process where it passed final evaluation in the fall of 2017 from among many other seedlings from the same cross and hundreds of other crosses. *Heuchera* 'Pink Panther' has been asexually propagated by division at the same nursery in Zeeland, Mich. in 2016 and by sterile, shoot-tip, tissue culture propagation, and the resultant plants have remained stable and continued to exhibit the same characteristics as the original plant for multiple generations.

The nearest comparison plant is the sister sibling 'Silver Gumdrop' U.S. Plant Pat. No. 29,207. 'Silver Gumdrop' has heavier and more consistent silver overlay on the foliage, the leaves are smaller and the flowers are more red. Compared to 'Wildberry' U.S. Plant patent application Ser. No. 16/350,491, 'Wildberry' has darker purple foliage with white flower petals. 'Electric Plum' U.S. Plant Pat. No. 29,924 has foliage that is more bright purple and the flowers are lighter pink on shorter stems with fewer flowers per stem. The ancestors differ in that 'Tiramisu' U.S. Plant Pat. No. 20,429 has leaves that are more butterscotch in color becoming more brick red and the flowers are cream-colored. 'Mocha Mint' (not patented) has smaller green leaves with silver overlay and fewer light-pink flowers on smaller stems. 'Milan' U.S. Plant Pat. No. 21,682 has smaller leaves that are more reddish with more green undertone. 'Stainless Steel' has leaves that are more silver with greenish undertone and without the greyed purple around the veins, and the flowers are white flowers.

Heuchera 'Pink Panther', differs from its parents as well as all other coral bells known to the applicant in the following combined traits:

1. The large foliage has rounded apices and rounded lobes.
2. Large leaf blades begin season pinkish coloration.
3. Leaf blades are shallowly dissected with apices rounded with tiny sharp tips and slightly ruffled margin.
4. Flowers provide a deep rose effect from calyces with pale pink petals.
5. Stiff, erect, branched panicles display flowers just above foliage beginning late spring.
6. The new plant is vigorous and produces large broadly-mounded clumps.

BRIEF DESCRIPTION OF THE DRAWINGS

The photographs of the new plant demonstrate the overall appearance of the plant including the unique traits. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
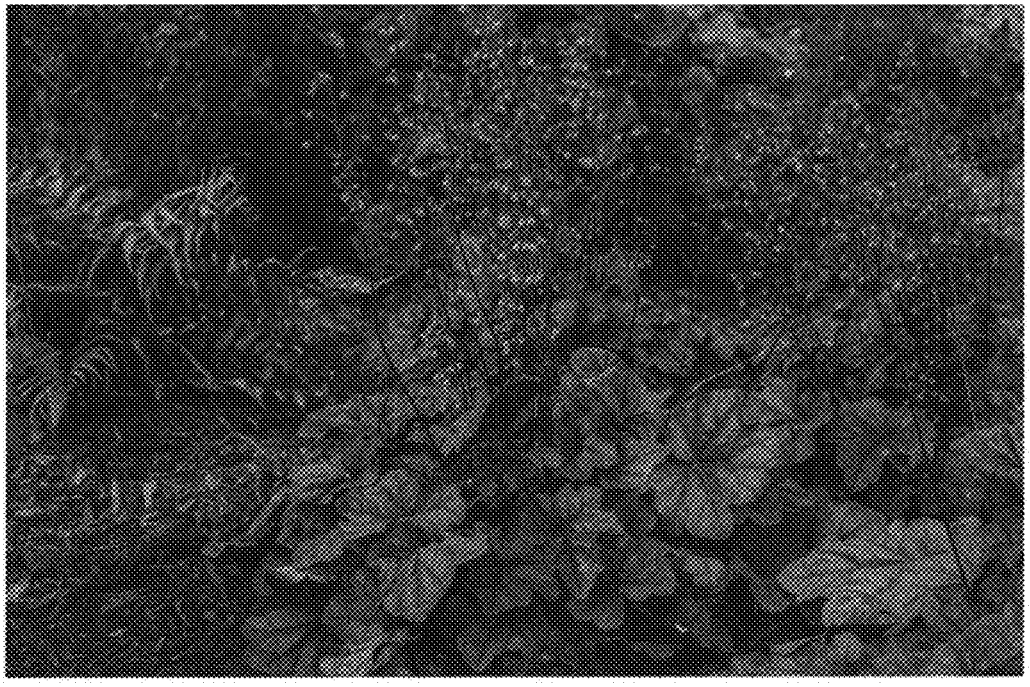
FIG. 1 shows a two-year-old plant in peak flowering.
Figure 2:
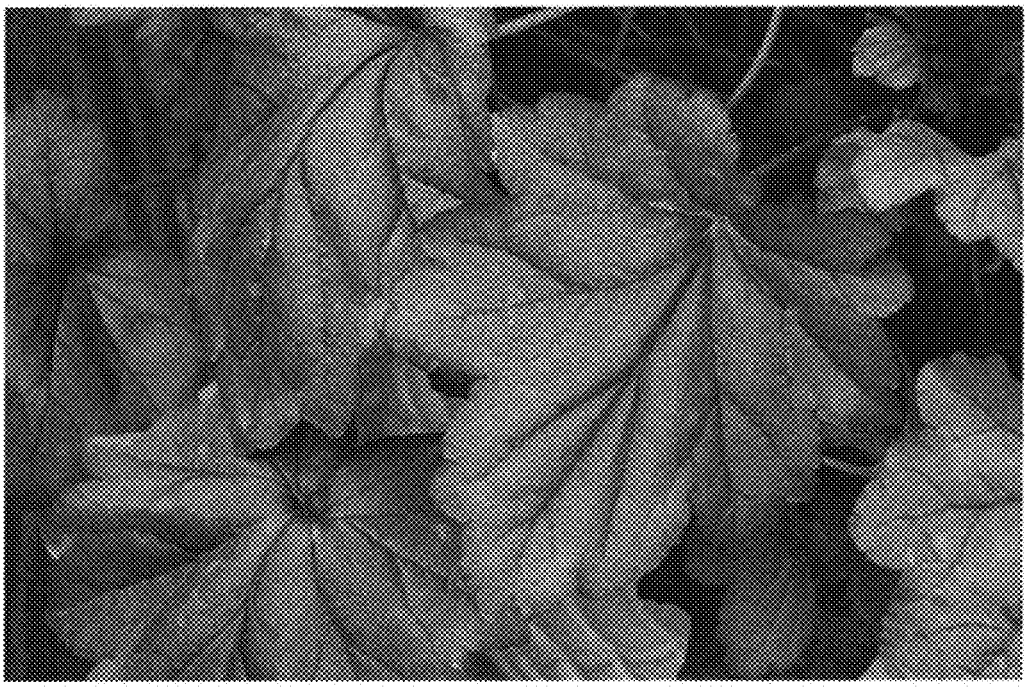
FIG. 2 shows a close-up of a flower panicle with buds and flowers from a one-year-old plant.

The following description is based on a two-year-old plant growing in a partially shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary teems are used.

Parentage: Female or seed parent was the unreleased proprietary hybrid 2-490-01 comprising 'Mocha' U.S. Plant Pat. No. 18,386, 'Tiramisu', 'Mocha Mint' along with 'Stainless Steel' U.S. Plant Pat. No. 23,349 in the ancestry, the male or pollen parent was the proprietary hybrid K11-52-15 comprising 'Milan' U.S. Plant Pat. No. 21,682 and 'Mocha Mint';

Plant habit: Hardy herbaceous perennial with basal rosette of foliage; dense broadly-mounded foliage about 36.0 cm tall and about 52.0 cm in diameter with scapes to about 57.0 cm long; with 10 stems per plant to about 7.0 cm long and 2.0 cm diameter at base, with about 14 to 16 leaves per stem; about 20 panicles per plant;

Roots: Fibrous, finely branched; color nearest RHS NN155B;

Growth rate: Rapid, rooting from cutting in two weeks and finishing in three-liter container in about two and a half months;

Foliage: Cordate; minutely puberulent adaxial and abaxial; palmately shallowly lobed with five main lobes dissected less than one-eighth of the way to petiole; apex and lobe apices rounded and mucronulate; base cordate with basal lobes nearly overlapping to overlapping about 0.5 cm; margins crenate to mucronulate, micro-ciliolate, weakly repand; lustrous and micro-puberulent abaxial and matte and sparsely puberulent adaxial; center flat; held upright near plant center to arching in outer leaves;

Leaf blade size: To about 14.5 cm wide and 15.5 cm long, average about 13.0 cm wide and 13.5 cm long;

Leaf color: Young initially emerging leaves adaxial nearest blend between RHS N77C and RHS N77B, abaxial nearest blend between RHS N77C and RHS 187C; still expanding young leaves adaxial nearest blend between RHS N77B and RHS N77C between the veins and surrounding the veins between RHS N187A and RHS 202A, still expanding leaves abaxial between RHS N77A and RHS N79A; mature mid-season leaves adaxial variable between nearest RHS N187A surrounding the veins and the blend of RHS N77B and RHS N77C between the veins and other leaves or leaf portions with a blend between RHS N187A surrounding the veins and nearest RHS N77C blended with RHS 187C as a silver overlay between the veins, abaxial mature mid-season leaves nearest blend between RHS 187A and RHS N186C; fall and winter color adaxial variable, nearest RHS N79B blended with RHS N77C with partial silver overlay nearest RHS N187C between veins, fall and winter color abaxial between RHS N186B and RHS N186C;

Leaf quantity: Dense, about 150 per plant;

Veins: Palmate, hirsutulous abaxial and glabrous adaxial; costate abaxial, slightly impressed adaxial;

Vein color: Early emerging adaxial nearest RHS 187C proximally and RHS N77A distally, abaxial nearest RHS N186D; still expanding adaxial nearest RBS 174A proximally and RHS N186A distally, abaxial nearest RHS N186D; mid-season and flowering time main adaxial veins nearest RHS 174A proximally and RHS N186A distally, mid-season and flowering time main abaxial veins near petiole nearest RHS N186D and secondary veins near margin nearest RHS N186C; fall adaxial near petiole nearest RHS N187B and distally nearest RHS N187A, abaxial veins near petiole nearest blend of RHS N186D and RHS 186C and secondary veins near margin nearest RHS N186D;

Petiole: Terete, base amplexicaul; with pubescent hairs to about 0.2 mm long; to about 17.0 cm long and 3.5 mm wide before stipule; average about 15.0 cm long and about 3.0 mm diameter above stipule and 18.0 mm wide at base including stipule;

Petiole color: On early emerging leaves closer to RHS N186D than RHS 186A; on still expanding leaves nearest RHS 187A; flowering season mature leaf nearest RHS 187A; autumn season nearest RHS 187A;

Stipule: Flared at base of petiole; glaucous adaxial and abaxial with ciliolate margin; to about 2.0 cm long and about 18.0 mm wide at base; with two distal lateral projections of about 3.0 mm long in distal portion;

Stipule color: Young expanding leaf adaxial and abaxial nearest RHS 60C; mature leaf adaxial center with mixtures of RHS 146B and RHS 187C lateral margins nearest RHS 185D, abaxial nearest RHS N186C; lateral margin portions translucent;

Peduncle: Panicle; terete; stiff; pubescent; upright; densely branched; to about 57.0 cm long and 5.0 mm diameter at base, average about 52.0 cm tall and 4.5 mm diameter; about 20 per plant with up to about 345 flowers per panicle, average about 270; moderately-branched panicle with up to 22 branches up to about 5.0 cm long and 1.0 mm diameter decreasing distally, average 18 branches per panicle; lower branches about 45 degree above horizontal, becoming closer to 30 degrees above horizontal in distal 6.0 cm of panicle; flower density medium; with about 4 cauline leaves below flower, spaced about 7.5 cm apart;

Flowering longevity: Panicle effective for about three to four weeks; individual flowers about 5 days; self-cleaning;

Peduncle color: Nearest RHS 187C becoming nearest RHS 187A distally;

Cauline leaves: Palmate; coarsely dentate margin; puberulent abaxial and adaxial; petiolate; blade about 21.0 mm across and 20.0 mm long, petiole about 7.0 mm long and 5.0 mm wide with stipule; with pair of stipules at base about 5.0 mm long; cauline leaves, petiole and stipule decreasing distally to become bracts subtending peduncle branches; stipules lanceolate with acute apex, truncate base and ciliate margin;

Cauline leaf color: Adaxial and abaxial identical to mid-season leaf color; cauline leaf petiole nearest RHS 187A abaxial and adaxial, and stipule adaxial and abaxial blend between RHS 146B and RHS 187C;

Pedicel: Terete, pubescent to glandular; to about 5.0 mm long and 0.5 mm diameter, average about 3.0 mm long and 0.5 mm diameter; attitude outwardly to slightly upwardly;

Pedicel color: Nearest RHS 187C lightening with age;

Buds one day prior to opening: Ellipsoid; rounded apex and attenuate base; micro-glandular; about 5.5 mm long and 2.5 mm diameter;

Bud color one day prior to opening: Between RHS 178A and RHS 178B;

Flower: Perfect; campanulate; actinomorphic; about 7.0 mm long to tip of exserted style and 7.0 mm in diameter at corolla apex;

Flower attitude: Mostly outwardly;

Calyx: Base fused in proximal 2.5 mm to form hypanthium; micro-glandular abaxial, glabrous adaxial; about 5.5 mm long and 7.0 mm wide at apex;

Sepals: Five; lanceolate; rounded apex, fused in basal 2.5 mm; to about 5.0 mm long and 2.0 mm wide at fusion;

Sepal color: Abaxial apex nearest RHS 182A and middle nearest RHS N155B and base blend between RHS 179B and RHS 180B; adaxial apex and longitudinal middle blushed with nearest RHS 186A and base nearest RHS N155B;

Petals: Five; oblanceolate to spatulate; subacute apex and attenuate base; entire; glabrous abaxial and adaxial; about 5.0 mm long and 1.0 mm wide in middle;

Petal color: Abaxial and adaxial nearest RHS N155B with very faint blush of light pink nearest RHS 186B;

Androecium: Five adnate to adaxial sepal about 1.0 mm above base;

*Filaments*.—Five, thin, glabrous; about 2.5 mm long and less than 0.3 mm diameter; color nearest RHS NN155B.

*Anthers*.—Ellipsoidal, distinct, basifixed, longitudinal; about 0.5 mm long and about 0.3 mm across; color nearest RHS 166C.

*Pollen*.—Rare; color nearest RHS 17B.

Gynoecium: One, two-beaked; half-inferior; bifid style with pistil split at ovary; about 7.0 mm long;

*Style*.—Bifid; split apart at apex of ovary; exserted; about 3.5 mm long and about 0.5 mm diameter; color nearest RHS N66D proximally and RHS N155B distally.

*Stigma*.—Acute apex, about 0.1 mm diameter; color nearest RHS N155C.

*Ovary*.—Half-inferior, about 2.0 mm long and 2.0 mm diameter; ellipsoidal to globose, base rounded; color nearest RHS N66D.

Fruit: Small two-beaked capsule; about 3.0 mm long and 2.5 mm across; drying to blend between RHS 199A and RHS N199C;

Seeds: Abundant; slightly flattened ellipsoid; about 0.7 mm long, 0.5 mm across and about 0.3 mm thick; color nearest RHS 202A;

Disease and pest tolerance: The new plant grows best with ample moisture and drainage in either part sun or full shade. Cold hardy from USDA zones 4 to 9. Other resistance and tolerance outside of that normal for *Heuchera* is not known.

It is claimed:

1. The new and distinct *Heuchara* plant named 'Pink Panther' as herein described and illustrated.

* * * * *